United States Patent
Pei et al.

(10) Patent No.: US 7,245,965 B1
(45) Date of Patent: Jul. 17, 2007

(54) IMPLANTABLE CARDIAC DEVICE PROVIDING MODE SWITCHING AND AUTOMATIC ATRIAL SENSITIVITY CONTROL AND METHOD

(75) Inventors: Xing Pei, Thousand Oaks, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 511 days.

(21) Appl. No.: 10/465,364

(22) Filed: Jun. 18, 2003

(51) Int. Cl.
*A61N 1/08* (2006.01)

(52) U.S. Cl. .............. 607/9; 607/11; 607/14; 607/18; 607/28; 607/29; 128/901

(58) Field of Classification Search .............. 607/9, 607/11, 18, 14, 27–29; 128/901
See application file for complete search history.

(56) References Cited

U.S. PATENT DOCUMENTS

| | | | | |
|---|---|---|---|---|
| 4,363,325 A | * | 12/1982 | Roline et al. | 607/9 |
| 4,944,298 A | * | 7/1990 | Sholder | 607/14 |
| 5,133,350 A | * | 7/1992 | Duffin | 607/6 |
| 5,800,466 A | | 9/1998 | Routh et al. | 607/14 |
| 5,843,133 A | | 12/1998 | Routh et al. | 607/14 |
| 6,047,213 A | * | 4/2000 | Sirokman et al. | 607/9 |
| 6,112,119 A | * | 8/2000 | Schuelke et al. | 607/9 |
| 6,907,286 B1 | * | 6/2005 | Kroll et al. | 607/14 |
| 6,963,776 B2 | * | 11/2005 | Seim | 607/14 |
| 2004/0127947 A1 | * | 7/2004 | Kim et al. | 607/9 |
| 2004/0260352 A1 | * | 12/2004 | Reuter et al. | 607/28 |

FOREIGN PATENT DOCUMENTS

| | | |
|---|---|---|
| WO | WO 98/46306 | 10/1998 |
| WO | WO 98/46307 | 10/1998 |

* cited by examiner

*Primary Examiner*—Carl Layno
*Assistant Examiner*—Deborah Malamud

(57) ABSTRACT

An implantable cardiac stimulation device, mode switchable between atrial tracking and atrial non-tracking pacing modes includes a threshold control for controlling atrial sensing threshold. The threshold control reduces the sensing threshold from a first threshold used during the atrial tracking pacing mode to a second threshold between the first threshold and the noise for use during the atrial non-tracking pacing mode. The necessity for readjusting the atrial sensing threshold is based upon the ratio of the sensing threshold and atrial amplitudes or upon a diagnostic distribution of atrial amplitudes.

27 Claims, 4 Drawing Sheets

IMPLANTABLE CARDIAC DEVICE PROVIDING MODE SWITCHING AND AUTOMATIC ATRIAL SENSITIVITY CONTROL AND METHOD

FIELD OF THE INVENTION

The present invention generally relates to an implantable cardiac device. The present invention more particularly relates to a mode switching implantable pacemaker capable of automatic atrial sensing threshold control to prevent atrial under-sensing, atrial over-sensing, and mode switch oscillation.

BACKGROUND OF THE INVENTION

The invention provides an implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

A popular mode of operation for dual-chamber pacemakers is the DDD mode. Specifically, DDD systems provide atrial pacing during atrial bradycardia, ventricle pacing during ventricular bradycardia, and atrial and ventricular pacing during combined atrial and ventricular bradycardia or heart block also known as AV block. In addition, DDD systems provide an atrial synchronous (atrial tracking) mode. This enables ventricular activity to track atrial activity to more closely approximate the normal response to exercise, or other physiological activity demanding a faster heart rate, by permitting a rate increase to occur commensurate with the rate of the sensed P waves. This advantageously increases cardiac output and facilitates maintenance of AV synchrony.

Atrial fibrillation is a common atrial tachyarrhythmia. Although it is not life threatening, it is associated with strokes thought to be caused by blood clots forming in areas of stagnant blood flow as a result of prolonged atrial fibrillation. Symptoms of atrial fibrillation may include heart palpitations and dizziness.

Atrial fibrillation can occur suddenly. It results in rapid and chaotic activity of the atria of the heart. The chaotic atrial activity in turn causes the ventricular activity to become rapid and variable. It is an extreme environment in which to properly pace the heart in a tracking mode. Hence, it is particularly important for pacemakers to include mode switching for switching from an atrial tracking mode to an atrial non-tracking mode.

Automatic mode switching (AMS) is intended to limit excessive pacing in the ventricles, due to atrial tachycardia or fibrillation, by switching from an atrial tracking pacing mode to an atrial non-tracking pacing mode. During AMS, the system will pace at a constant rate in the ventricles if it is not inhibited by an intrinsic ventricular sensed event. AMS addresses the problem of potential excessive ventricular pacing at some cost. At the time of a mode switch, the ventricular pacing rate drops to the programmed AMS rate, which is often much lower than the current pacing rate. During an episode of atrial fibrillation, the electrical signals from the atria often become small and highly variable, increasing the incidence of inappropriate sensing with the fixed atrial sensitivity setting previously determined during normal sinus rhythm. Due to the inappropriate atrial sensing, the pacing system can easily fall in and out of the atrial non-tracking mode and atrial-tracking mode. This is a mode switch oscillation. The result is that the patient is alternately paced at higher ventricular rates when the system is out of the atrial non-tracking mode and at a much lower ventricular rate when it is in the non-tracking mode. This increases patient morbidity.

The present invention eliminates mode switch oscillation due to inappropriate sensing. By automatic adjustment of atrial sensitivity to appropriate levels during mode switch, mode switch oscillation is avoided. This reduces the discomfort of patients and improves their quality of life.

SUMMARY

What is described herein is an implantable cardiac stimulation device comprising an atrial channel including a sensing circuit, having a threshold, that senses atrial activity of a heart and provides an atrial activity signal, an arrhythmia detector, responsive to the atrial activity signal, that detects an atrial tachyarrhythmia and a pacing circuit that paces the heart in an atrial non-tracking mode responsive to the arrhythmia detector detecting an atrial tachyarrhythmia and an atrial tracking mode absent detection of an atrial tachyarrhythmia. The device further comprises a noise measuring circuit that measures a noise level in the atrial channel and a threshold control that reduces the sensing threshold from a first threshold to a second threshold between the first threshold and the noise level when the pacing circuit transitions from the atrial tracking mode to the atrial non-tracking mode.

The device preferably periodically adjusts the second threshold. The device may further comprise a processor that produces a distribution of sensed atrial event amplitudes. The threshold control may then set the second threshold based upon the distribution. Where the distribution is bi-modal, the threshold control preferably sets the second threshold to a level between the peaks of the bi-modal distribution. Where the distribution is mono-modal, the threshold control may set the second threshold to a level between noise and a percentage of atrial amplitudes.

The threshold control preferably resets the first threshold when the pacing circuit transitions from the atrial non-tracking mode to the atrial tracking mode. The threshold control preferably resets the first threshold to a level related to atrial activity amplitudes. The device may further comprise a processor that provides a distribution of atrial activity amplitudes. The threshold control may then reset the first threshold to a level related to the atrial activity amplitude distribution.

The invention further provides an implantable cardiac stimulation device comprising sensing means for sensing atrial activity of a heart and providing an atrial activity signal, the sensing means having a threshold, arrhythmia detecting means, responsive to the atrial activity signal for detecting an atrial tachyarrhythmia, noise level measuring means for measuring atrial activity noise sensed by the sensing means, and stimulation means for pacing the heart in an atrial non-tracking mode responsive to detection of an atrial tachyarrhythmia and an atrial tracking mode absent detection of an atrial tachyarrhythmia. The device further comprises threshold control means for reducing the sensing threshold from a first threshold to a second threshold between the first threshold and the measured noise when the stimulation means transitions from the atrial tracking mode to the atrial non-tracking mode.

The invention still further provides a method for controlling atrial sensitivity threshold in an implantable cardiac stimulation device. The method comprises the steps of sensing atrial activity of a heart with a sensing circuit having a threshold to provide an atrial activity signal, responsive to the atrial activity signal, detecting for an atrial tachyarrhythmia, pacing the heart in an atrial non-tracking mode responsive to detection of an atrial tachyarrhythmia and an atrial tracking mode absent detection of an atrial tachyarrhythmia, measuring atrial activity noise, and reducing the sensing threshold from a first threshold to a second threshold between the first threshold and the measured noise when transitioning from the atrial tracking mode to the atrial non-tracking mode.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
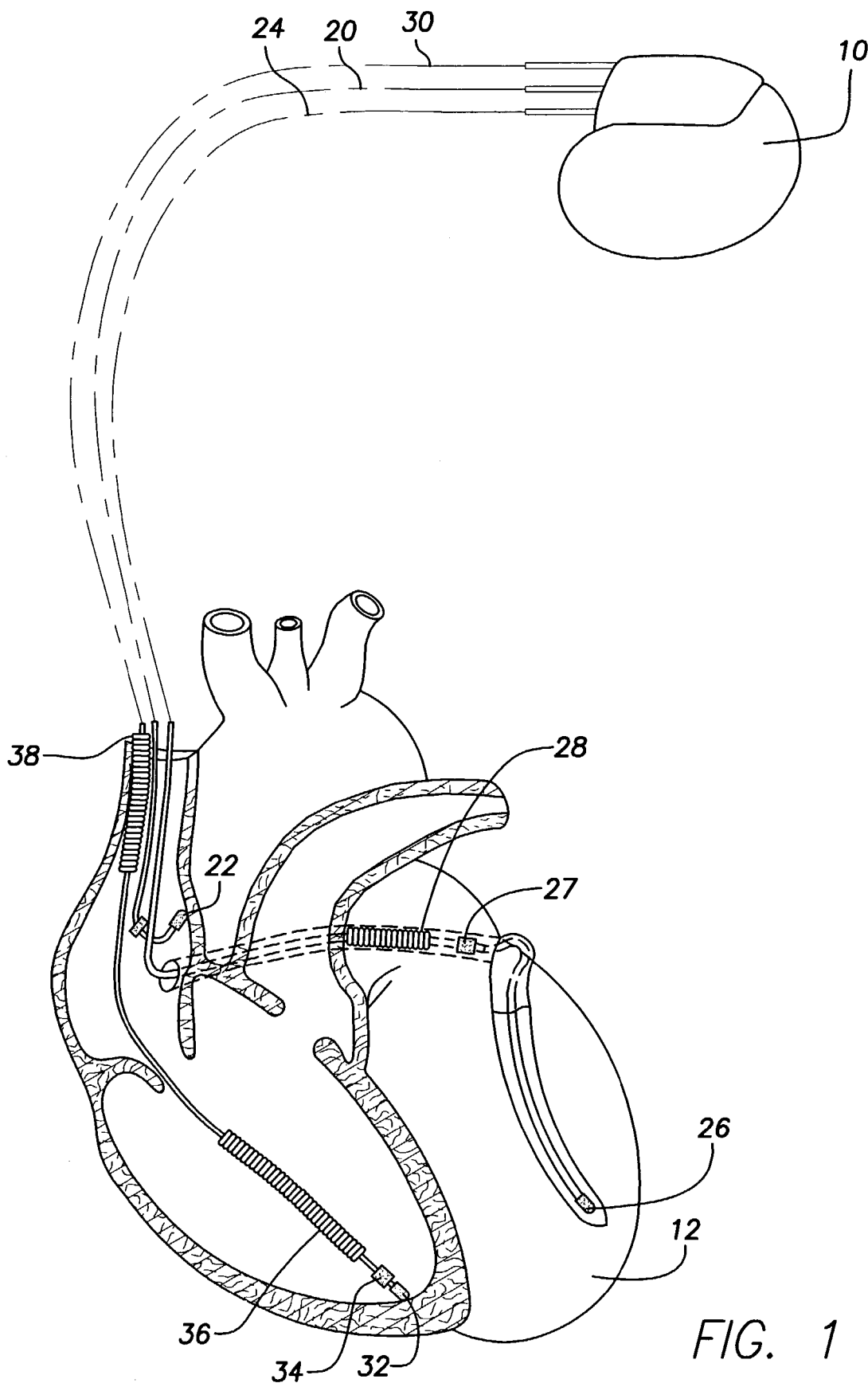
FIG. 1 is a simplified diagram illustrating an implantable stimulation device embodying the present invention in electrical with a heart by three leads implanted in the heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
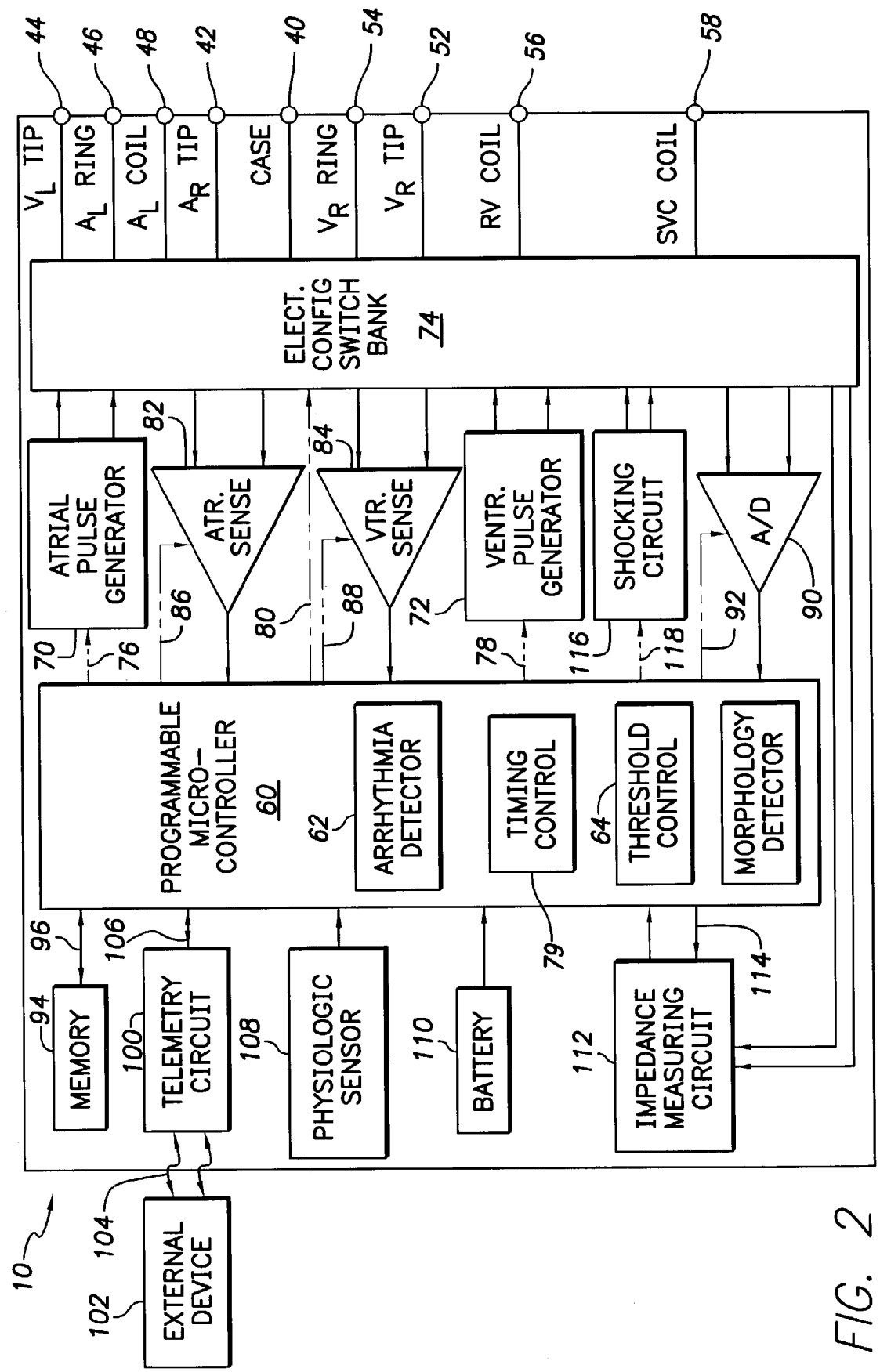
FIG. 2 is a functional block diagram of the implantable stimulation device of FIG. 1 illustrating the basic elements thereof to provide cardioversion, defibrillation and pacing stimulation in all four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art. As will be seen subsequently, the present invention is particularly directed to threshold control of atrial sensing circuit 82.

For arrhythmia detection, the device 10 increases an arrhythmia detector 62 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 62 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, atrial tracking pacing, atrial non-tracking pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, this description shall now turn to those aspects of the device 10 which are particularly relevant to the present invention. As previously described, the device 10 may be programmed to provide dual chamber, atrial tracking pacing therapy. However, should the arrhythmia detector 62 detect an atrial tachyarrhythmia, such as atrial tachycardia or atrial fibrillation, the device will mode switch to a dual chamber, atrial non-tracking mode, wherein the ventricles are paced on demand at a reduced and constant rate, disassociated from the atrial activity. This avoids a high ventricular rate which would result if the ventricular pacing were to track the high and variable intrinsic atrial rate during the atrial tachyarrhythmia.

Also during atrial tachyarrhythmias, the amplitudes of the atrial activity markedly decrease and become highly variable. Hence, the atrial sensing threshold used prior to the mode switch may result in not sensing some atrial events (under-sensing) making the atrial rate appear to be less than it actually is. This could cause the device to switch its pacing mode back to the atrial tracking mode resulting in a sudden increase in ventricular rate. This mode switching oscillation could continue until the atrial tachyarrhythmic episode terminates.

To preclude such mode switching oscillation, the device 10, in accordance with the present invention, includes a threshold control 64 which automatically controls the threshold of the atrial sensing circuit 82 over control line 86. Basically, the threshold control, if needed, reduces the threshold of the atrial sensing circuit 82 from a first or pre-programmed threshold existing just prior to the mode switch, to a second or mode switched threshold after the transition to the atrial non-tracking pacing mode.

In accordance with a first embodiment, the atrial sensing threshold is periodically adjusted based upon the maximum P wave amplitude providing an indication of under-sensing. Also relevant to the adjustment is the noise in the sensed atrial activity. The control 64 preferably sets the atrial sensing threshold to a level greater than the noise to avoid over-sensing.

First, when the device is implanted, the atrial sensing threshold is set to an initial or first threshold ($Th_i$). Periodically, the noise level (noise) is sensed during a noise sensing window with the atrial sense amplifier 82 during a time in which there should not be any cardiac activity. A temporary threshold ($Th_t$) is then calculated by expression (a) below:

$$Th_t = A(Th_i - \text{noise}) + \text{noise} \tag{a}$$

where A may be 0.5, for example.

This will ensure that the sensing threshold will always be less than $Th_i$ and greater than the noise. This threshold value ($Th_t$) is used as a reference for threshold determination during the mode switch.

Next, it is determined if there should be a change to the temporary threshold ($Th_t$). As will be seen hereinafter, the temporary threshold is adjusted if necessary periodically during atrial tracking pacing (when the device is not mode switched). In addition, the $Th_i$ may be adjusted to ensure proper sensing of the P waves for atrial tracking pacing to avoid over or under-sensing.

After the arrhythmia detector 62 detects an atrial tachyarrhythmia, the device mode switches to an atrial non-tracking mode, and the sensing threshold is initially reduced, if necessary, to the ($Th_t$) as previously determined. Once in the mode switch, a small atrial sense window is started to measure amplitudes of each atrial sensed event sensed with the last established temporary sensing threshold. The maximum and minimum amplitudes are determined. If the ratio of the current sensing threshold ($Th_c$) to the maximum atrial event amplitude (A max) is greater than Z, where Z may be 0.5, for example, the probability of under-sensing is confirmed and the sensing threshold during the mode switch may be reduced again. Otherwise, it is left unchanged.

The sensing threshold during the mode switch is adjusted from the current temporary sensing threshold ($Th_c$) to a second sensing threshold referred to herein as the mode switch threshold ($Th_{ms}$). It is determined by expression (b) below:

$$Th_{ms}=B(Th_c-\text{noise})+\text{noise} \quad\quad (b)$$

Expression (b) ensures that the new reduced threshold is less than the current temporary threshold and greater than the noise. Thereafter, the mode switch threshold is periodically adjusted if necessary.

When the atrial tachyarrhythmia episode terminates, the arrhythmia detector 62 detects an absence of the atrial arrhythmia and the device switches back or returns to an atrial tracking pacing mode. After the return, the sensing threshold is increased to avoid over-sensing. The sensing threshold may be returned to the initially programmed sensing threshold. Alternatively, the sensing threshold may be returned to a threshold value set just before the mode switch occurred. Alternatively, the sensing threshold may be set to a value between the last current temporary threshold ($Th_c$) and the value before the mode switch occurred or the initial programmed threshold and then modified. Still further, the sensing threshold may be set to a level between the noise and a percentage of atrial amplitudes, such as the atrial peaks.

A more robust method of controlling the sensing threshold would be to produce a distribution of the atrial activity amplitudes. The threshold is adjusted to avoid over-sensing so that a percentage of the atrial activity is above the threshold. A bimodal distribution is an indication of over-sensing. The threshold should be set between the two peaks. These will set the threshold to a level between the threshold before mode switch and noise. If the distribution is monomodal and ranging from the noise to the previous threshold, the threshold should be set to a level which is a percentage of atrial peaks.

The method may be made still more robust by using the processor 60 to generate a histogram of the atrial amplitudes. Once in mode switch, the amplitudes are sorted into a diagnostic data array. After N events, the distribution is calculated periodically or continuously. If it is bimodal, there is over-sensing present. The threshold is again set to a level between the two peaks. If the distribution is monomodal, the threshold is adjusted to a level of a percentage of the atrial activity peaks.

The foregoing distributions may also be used when the device transitions back to the atrial tracking pacing mode. If the distribution is bimodal, the threshold is returned to a level between the two peaks.

Figures 1, 3:
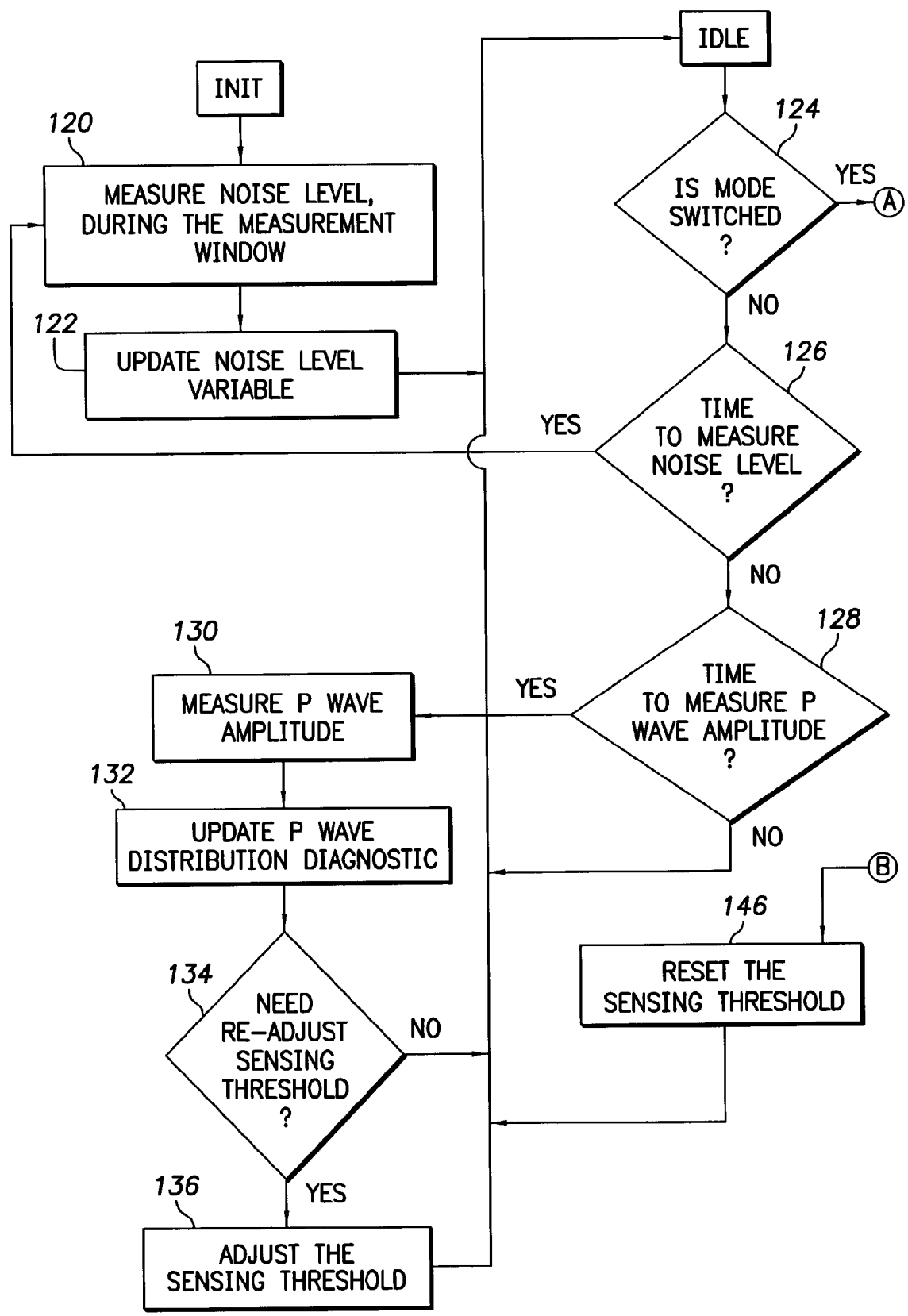
FIG. 3 is a flow chart describing an overview of the operation of one embodiment of the present invention.
Figures 2, 3:
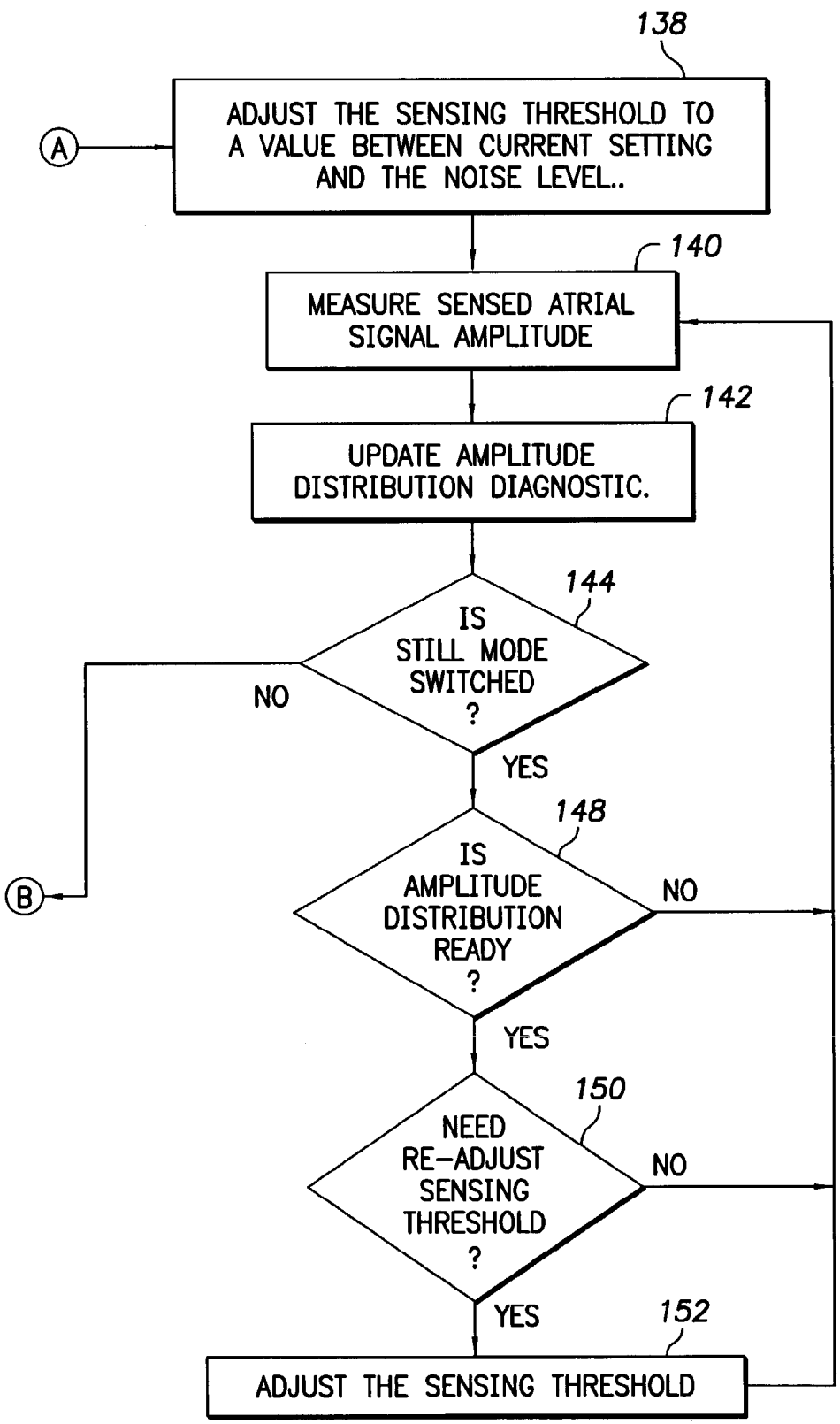

In FIG. 3, a flow chart is shown describing an overview of the operation and novel features implemented in one embodiment of the device 10 in accordance with the present invention. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with activity block 120 wherein the threshold control 64 measures the atrial noise level during atrial noise level measurement windows. The process then advances to activity block 122 wherein the noise level is updated by the processor 60.

Following the measurement of the noise level, the process advances to decision block 124 wherein the threshold control 64 determines if the arrhythmia detector 62 has detected an atrial tachyarrhythmia and the device has mode switched from an atrial tracking pacing mode to an atrial non-tracking pacing mode. If the device has not mode switched, the process then advances to decision block 126 wherein it is determined if it is now time to measure noise once again. If it is time to measure noise, the process advances to activity bock 120 for measuring the noise level as previously described. If it is not time to measure atrial activity noise, the process advances to decision block 128 wherein it is determined if it is time to measure atrial amplitudes. If it is time to measure atrial amplitudes, the process advances to activity block 130 wherein the current atrial amplitude or P wave is measured. The process then advances to activity block 132 where the P wave amplitude measurement is added to the diagnostic distribution. Following activity block 132, the process advances to decision block 134 wherein it is determined if adjustment in the atrial sensing threshold is required. The criteria for such a decision have been previously described. Adjustment may be considered necessary if the ratio of the current sensing threshold to the maximum P wave amplitude is greater than a given percentage, or determined with P wave amplitude distribution. If it is, the process advances to activity block 136 wherein the sensing threshold is adjusted to a new temporary threshold. If adjustment is not necessary, the process returns to decision block 124.

If in decision block 124 it is determined that the device has mode switched to an atrial non-tracking pacing mode, the process advances to activity block 138 wherein the atrial sensing threshold is adjusted to a value between the current temporary sense threshold and the noise level. Following activity block 138, the process advances to activity block 140 wherein the sensed atrial signal amplitude is measured and then used in activity block 142 for updating the amplitude diagnostic distribution during mode switch.

After activity block 142, the process then advances to decision block 144, wherein the threshold control 64 determines if the device is still in mode switch. If the device is not in mode switch, indicating that the arrhythmia detector 62 has detected an absence of the atrial tachyarrhythmia and that the device has transitioned back to an atrial tracking pacing mode, the process advances to activity block 146 wherein the sensing threshold is reset. As previously described, the sensing threshold may be reset to the initially programmed sensing threshold, the last temporary sensing threshold, or a sensing threshold based upon atrial activity level and noise. The process then returns to decision block 124.

If in decision block 144 it is determined that the device is still in an atrial non-tracking pacing mode, the process advances to decision block 148 wherein it is determined if the amplitude distribution is ready. Here, as previously described, the device maintains a histogram of atrial amplitudes. When N number of amplitudes have been stored in the distribution, the amplitude distribution is considered to be ready. If the amplitude distribution is not ready, the process returns to activity block 140 for the taking of another atrial signal amplitude measurement. If, however, the amplitude distribution is ready, the process advances to activity block 150 to determine if there is a need to adjust the sensing threshold. Here, the distribution is analyzed to determine if it is bimodal or mono-modal. If it is bimodal, indicating that there is over-sensing, the process advances to activity block 152 wherein the atrial sensing threshold is adjusted to a level between the two distribution peaks. The process then returns to activity block 140.

As can be seen from the foregoing, the present invention provides an implantable cardiac stimulation device which is capable of mode switching from an atrial tracking pacing mode to an atrial non-tracking pacing mode. The atrial sensing threshold is continuously automatically controlled to avoid under-sensing during the atrial non-tracking pacing mode to avoid mode switch oscillation. Further, the atrial sensing threshold is controlled during the atrial tracking pacing mode to assure that there is no over-sensing or under-sensing of atrial activity.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   an atrial sensing circuit that senses atrial activity of a heart and provides an atrial activity signal, the sensing circuit having an adjustable sensitivity threshold;
   an arrhythmia detector, responsive to the atrial activity signal, that detects an atrial tachyarrhythmia;
   a pacing circuit that paces the heart in an atrial non-tracking mode responsive to the arrhythmia detector detecting an atrial tachyarrhythmia and an atrial tracking mode absent detection of an atrial tachyarrhythmia;
   a noise level measuring circuit that measures a noise level in the atrial sensing circuit; and
   a threshold control that immediately reduces the sensitivity threshold from a first threshold to a second threshold between the first threshold and the noise level when the pacing circuit transitions from the atrial tracking mode to the atrial non-tracking mode;
   wherein the threshold control immediately reduces the sensitivity threshold from the first threshold to the second threshold irrespective of whether the atrial sensing circuit senses P-waves immediately after the pacing circuit transitions from the atrial tracking mode to the atrial non-tracking mode;
   wherein the threshold control sets the sensitivity threshold to the second threshold while operating in the atrial-non-tracking pacing mode to preclude mode switch oscillation;
   wherein the first threshold is $Th_t$, wherein the second threshold is $Th_c$, and wherein $Th_c = A(Th_t - noise) + noise$; and wherein A is a predetermined constant.

2. The device of claim 1 wherein the threshold control periodically adjusts the second threshold.

3. The device of claim 1 further comprising a processor that produces a distribution of sensed atrial event amplitudes and wherein the threshold control sets the second threshold based upon the distribution.

4. The device of claim 3 wherein the threshold control sets the second threshold to a level between peaks of a bi-modal distribution.

5. The device of claim 3 wherein the threshold control sets the second threshold to a level between noise and a given percentage of atrial amplitudes when the distribution is mono-modal.

6. The device of claim 1 wherein the threshold control resets the first threshold when the pacing circuit transitions from the atrial non-tracking mode to the atrial tracking mode.

7. The device of claim 6 wherein the threshold control resets the first threshold to a level related to atrial activity amplitudes.

8. The device of claim 6 further comprising a processor that provides a distribution of atrial activity amplitudes, and wherein the threshold control resets the first threshold to a level related to the atrial activity amplitude distribution.

9. The device of claim 1 wherein the second threshold is further adjusted to a subsequent threshold, wherein the subsequent threshold is $Th_{ms}$, wherein $Th_{ms} = B(Th_c - noise) + noise$, and wherein B is a predetermined constant.

10. An implantable cardiac stimulation device comprising:
    sensing means for sensing atrial activity of a heart and providing an atrial activity signal, the sensing means having an adjustable sensitivity threshold;
    arrhythmia detecting means, responsive to the atrial activity signal, for detecting an atrial tachyarrhythmia;
    a stimulation means for pacing the heart in an atrial non-tracking mode responsive to detection of an atrial tachyarrhythmia and an atrial tracking mode absent detection of an atrial tachyarrhythmia;
    noise level measuring means for measuring atrial activity noise sensed by the sensing means; and
    threshold control means for immediately reducing the sensitivity threshold from a first threshold to a second threshold when the stimulation means transitions from the atrial tracking mode to the atrial non-tracking mode;
    wherein the threshold control means immediately reduces the sensitivity threshold from the first threshold to the second threshold irrespective of whether the sensing means senses P-waves immediately after the stimulation means transitions from the atrial tracking mode to the atrial non-tracking mode;
    wherein the threshold control means sets the sensitivity threshold to the second threshold while operating in the atrial-non-tracking pacing mode to preclude mode switch oscillation;
    wherein the first threshold is $Th_t$, wherein the second threshold is $Th_c$, and wherein $Th_c = A(Th_t - noise) + noise$; and wherein A is a predetermined constant.

11. The device of claim 10 wherein the threshold control means includes means for periodically adjusting the second threshold.

12. The device of claim 10 further comprising processing means for producing a distribution of sensed atrial event amplitudes and wherein the threshold control means includes means for setting the second threshold based upon the distribution.

13. The device of claim 12 wherein the threshold control means sets the second threshold to a level between peaks of a bi-modal distribution.

14. The device of claim 12 wherein the threshold control means sets the second threshold to a level between noise and a percentage of atrial amplitudes when the distribution is mono-modal.

15. The device of claim 10 wherein the threshold control means includes means for resetting the first threshold when the stimulation means transitions from the atrial non-tracking mode to the atrial tracking mode.

16. The device of claim 15 wherein the threshold control means resets the first threshold to a level related to atrial activity amplitudes.

17. The device of claim 15 further comprising a processor for providing a distribution of atrial activity amplitudes, and wherein the threshold control means includes means for resetting the first threshold to a level related to the atrial activity amplitude distribution.

18. The device of claim 10 wherein the second threshold is further adjusted to a third threshold, wherein the third threshold is $Th_{ms}$, wherein $Th_{ms}=B(Th_c-noise)+noise$, and wherein B is a predetermined constant.

19. In an implantable cardiac stimulation device, a method comprising:
sensing atrial activity of a heart with a sensing circuit to provide an atrial activity signal, wherein the sensing circuit comprises an adjustable sensitivity threshold;
monitoring the atrial activity to detect an atrial tachyarrhythmia;
pacing the heart in an atrial non-tracking mode responsive to detection of an atrial tachyarrhythmia and in an atrial tracking mode absent detection of an atrial tachyarrhythmia;
measuring noise in the sensing circuit; and
immediately reducing the sensitivity threshold from a first threshold to a second threshold between the first threshold and the measured noise when transitioning from the atrial tracking mode to the atrial non-tracking mode;
wherein the sensitivity threshold is immediately reduced from the first threshold to the second threshold irrespective of whether P-waves are sensed immediately after the pacing circuit transitions from the atrial tracking mode to the atrial non-tracking mode;
wherein the sensitivity threshold is reduced to the second threshold while operating in the atrial-non-tracking pacing mode to preclude mode switch oscillation;
wherein the first threshold is $Th_t$, wherein the second threshold is $Th_c$, and wherein $Th_c=A(Th_t-noise)+noise$; and wherein A is a predetermines constant.

20. The method of claim 19 wherein comprising the further step of periodically adjusting the second threshold.

21. The method of claim 19 comprising the further steps of producing a distribution of sensed atrial amplitudes and setting the second threshold based upon the distribution.

22. The method of claim 21 wherein the setting step includes adjusting the second threshold to a level between peaks of a bi-modal distribution.

23. The method of claim 21 wherein the setting step includes adjusting the second threshold to a level between noise and a percentage of atrial amplitudes when the distribution is mono-modal.

24. The method of claim 19 comprising the further step of resetting the first threshold when transitioning from the atrial non-tracking mode to the atrial tracking mode.

25. The method of claim 24 wherein the resetting step includes adjusting the first threshold to a level related to atrial activity amplitudes.

26. The method of claim 24 comprising the further steps of providing a distribution of atrial activity amplitudes, and resetting the first threshold to a level related to the atrial activity amplitude distribution.

27. The method of claim 19 wherein the second threshold is further adjusted to a third threshold, wherein the third threshold is $Th_{ms}$, wherein $Th_{ms}=B(Th_c-noise)+noise$, and wherein B is a predetermined constant.

* * * * *